(12) United States Patent
Duflot et al.

(10) Patent No.: US 6,204,378 B1
(45) Date of Patent: *Mar. 20, 2001

(54) METHOD FOR PRODUCING PALATINITOL

(75) Inventors: Pierrick Duflot, Lacouture; Catherine Fouache, Sailly Labourse, both of (FR)

(73) Assignee: Roquette Freres, Lestrem (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,721
(22) PCT Filed: Nov. 14, 1996
(86) PCT No.: PCT/FR96/01797
  § 371 Date: Sep. 12, 1997
  § 102(e) Date: Sep. 12, 1997
(87) PCT Pub. No.: WO97/19093
  PCT Pub. Date: May 29, 1997

(30) Foreign Application Priority Data

Nov. 17, 1995 (FR) .................................................. 95 13648

(51) Int. Cl.$^7$ ............................... C07H 1/00; C07H 3/00; C07C 31/18; A23G 3/00
(52) U.S. Cl. .................... 536/125; 536/123; 536/123.13; 536/124; 568/852; 568/861; 568/863; 426/658
(58) Field of Search ............................... 536/123, 123.13, 536/124, 125; 568/852, 861, 863; 426/658

(56) References Cited

U.S. PATENT DOCUMENTS

| | | | |
|---|---|---|---|
| 4,117,173 | * 9/1978 | Schiweck et al. | 426/548 |
| 4,654,377 | * 3/1987 | Möhring et al. | 521/170 |
| 5,578,339 | * 11/1996 | Kunz et al. | 426/658 |

FOREIGN PATENT DOCUMENTS

| | | |
|---|---|---|
| 3403973 | * 8/1985 | (DE) . |
| 2515186 | 4/1983 | (FR) . |
| 63-96195 | 4/1988 | (JP) . |
| 63-162698 | 7/1988 | (JP) . |
| 4121198 | * 4/1992 | (JP) . |

OTHER PUBLICATIONS

Database WPI, Section Ch, Week 9225 Derwent Publications Ltd., London, GB; AN 92–203078 XP002010687 & JP 04 121 198 A, Abstract.

"Alternative Sweeteners" by Lyn O'Brien Nabors, Chap. 11, pp. 217–244, 1986.

Wolfrom et al., "Isomaltitol", *J. Amer. Chem. Soc.*, vol. 74: 1062–1064, Feb. 10, 1952.*

Straeter et al., "Isomalt", *Food Sci. Technol.*, vol. 48 (Altern. Sweeteners (2nd Ed.)): 309–332, 1991.*

Schiweck. "Palatinit—Technological Properties", Health Sugar Sub., Proc. ERGOB Conf. Sugar Substitutes, pp. 138–144 (Meeting date 1978), 1979.*

Gau et al., "Analytical characterization of Palatinit", *Z. Lebensm.—Unters. Forsch.*, vol. 168(2): 125–130, 1979.*

Kretchmer & Hollenbeck (Editors), *Sugars and Sweeteners*, CRC Press, pp. 141–143, 1991.*

* cited by examiner

*Primary Examiner*—Howard C. Lee
(74) *Attorney, Agent, or Firm*—Henderson & Sturm LLP

(57) ABSTRACT

A novel method for making palatinitol comprising a first step of epimerising isomaltose under conditions enabling a mixture of α-D-glucopyranosyl-(1→6)-D-mannose and isomaltose to be achieved, a second step of catalytically hydrogenating the mixture, and a third step of chromatographically depleting the isomaltitol in the hydrogenated mixture to give a roughly equimolecular mixture of α-D-glucopyranosyl-(1→6)-D-sorbitol and α-D-glucopyranosyl-(1→6)-D-mannitol.

4 Claims, No Drawings

METHOD FOR PRODUCING PALATINITOL

The present invention relates to a new process for producing palatinitol.

More particularly it relates to a production process for palatinitol starting from isomaltose or α-D-glucopyranosyl-(1→6)-D-glucose.

Palatinitol is a sweetening agent of low caloric mass and low cariogenicity which up to now is obtained by catalytic hydrogenation at neutral pH of isomaltulose or α-D-glucopyranosyl-(1→6)-D-fructose.

Isomaltulose is itself obtained by enzymatic isomerization, using a saccharose glysosyl transferase, saccharose or α-D-glucopyranosyl-(1→2)-β-D-fructofuranoside.

Therefore, it is saccharose which constitutes the raw material for obtaining palatinitol, a mixture containing roughly equimolecular proportions of α-D-glucopyranosyl-(1→6)-D-sorbitol (GPS or isomaltitol) and α-D-glucopyranosyl-(1→6)-D-mannitol (GPM).

Palatinitol, which is also called isomalt, is in particular marketed by the Company Süddeutsche Zucker AG under the name Palatinit®.

Among other documents which concern the obtaining and properties of palatinitol the following work can be referred to: "Alternative Sweeteners" published in 1986 by LYN O'BRIEN NABORS, chapter 11, pages 217 to 244.

Concerned to develop a process which allows palatinitol to be obtained from a raw material other than saccharose, the Applicant Company has noticed that this goal could be achieved by a process using isomaltose or α-D-glucopyranosyl-(1→6)-D-glucose.

In accordance with the present invention, palatinitol is obtained thanks to a process characterized in that in a first stage, the epimerization of isomaltose is carried out under conditions which allow a mixture of α-D-glucopyranosyl-(1→6)-D-mannose and isomaltose to be obtained, in a second stage, catalytic hydrogenation is carried out on this mixture.

in a third stage, chromatographic depletion of the isomaltitol in this hydrogenated mixture is carried out so as to obtain a roughly equimolecular mixture of α-D-glucopyranosyl-(1→6)-D-sorbitol and α-D-glucopyranosyl-(1→6)-D-mannitol If it is reasonable to imagine that palatinitol may be obtained from saccharose, the person skilled in the art could in no way expect that this same palatinitol might be obtained from isomaltose, which is obtained from glucose and thus from diverse and various starches.

In fact, in the first case, saccharose, the structural formula of which includes a fructose unit, will produce, in a known fashion by enzymatic isomerization, the corresponding ketose i.e. isomaltulose.

And it is known to the person skilled in the art that the hydrogenation of such a ketose leads to the formation of the two corresponding itols in approximately equimolecular proportions. Therefore, the fact that the formula of saccharose is related to that of palatinitol allows the result to be anticipated.

However, the process according to the invention does not implement a starting product whose formula is related to that of the sought palatinitol. In fact, isomaltose as well as glucose and starch, have a structure which does not contain a fructose unit and is therefore far from being related to that of palatinitol.

The process according to the invention therefore allows freedom from the requirement to use saccharose as raw material for the production of palatinitol since isomaltose can be easily obtained from glucose and therefore from diverse and varied starches, whether they originate from cereals or tubers.

A process for obtaining isomaltose from glucose or a corn syrup is described, for example, in the French Patent Application 2,515,186.

In the process according to the invention, it is preferred to use crystallized isomaltose, although syrups which are very rich in isomaltose are also suitable if one accepts that maltitol or isomaltotriitol may be present in the palatinitol. The two last-named compounds originate from the hydrogenation of maltose or isomaltotriose which represent the main impurities in syrups which are very rich in isomaltose.

In the process according to the invention, the epimerization of isomaltose can be carried out as described in the Japanese Patent Application 63-162698 using a metallic salt and an amine but it is preferably carried out in the manner described in the Japanese Patent Application 63-96195 and which consists of reacting an aqueous solution of isomaltose, at a pH comprised between 2.5 and 4, in the presence of molybdic anhydride or hexavalent molybdenum salts, at a temperature comprised between 90° C. and 140° C.

Preferably, ammonium molybdate is used in a proportion of approximately 0.1 to 1.5% by weight relative to the isomaltose.

More preferably, the epimerization of isomaltose is carried out in the form of an aqueous sweetened solution containing 10 to 70% isomaltose.

The epimerization conditions are adjusted (essentially the catalyst content, the duration of epimerization and the reaction temperature) so as to obtain a mixture of isomaltose and α-D-glucopyranosyl-(1→6)-D-mannose, containing 10 to 40% of the latter compound. It is not economical to treat mixtures containing less than 10% of this compound, and mixtures containing more than 40% of it contain too many impurities which form under the extreme conditions of epimerization.

It is preferred to operate under conditions which allow 20 to 35% of α-D-glucopyranosyl-(1→6)-D-mannose to be obtained and yet more preferably from 25 to 35% of this compound.

The mixture obtained in this way is then demineralized on ion exchange resins in order to remove the salts which have been used as the catalyst.

In the process according to the invention hydrogenation of the epimerized mixture is carried out in a manner known per se, continuous or discontinuous, under a hydrogen pressure of 30 to 200 bars, at a temperature of 80 to 150° C. in the presence of a nickel- or ruthenium-based catalyst and at a pH close to neutral. Hydrogenation carried out at a pH of less than 4.0 will result in partial hydrolysis of the isomaltose into glucose and the α-D-glucopyranosyl-(1→6)-D-mannose into glucose and mannose with the appearance of sorbitol and mannitol. Hydrogenation at a pH higher than 9 will produce a result which is not desired, the formation of GPS and not GPM from the α-D-glucopyranosyl-(1→6)-D-mannose. In a general fashion, the hydrogenation is carried out until the content of the reducing sugars, measured by the Bertrand method, becomes lower than 1% and preferably, lower than 0.5%.

After the hydrogenation stage, the syrups obtained are purified to remove the catalyst by filtration then demineralization on ion exchange resins and these syrups are concentrated to a dry matter content comprised between 10 and 70% with a view to their chromatography. These hydrogenated syrups thus show an average composition ranging from 10 to 40% of GPM and from 60 to 90% of GPS. Syrups are preferred which contain from 25 to 35% of GPM and from 65 to 75% of GPS.

In the process of the invention, depletion of the hydrogenated syrups in GPS by chromatographic route is then carried out.

As a rule, when a chromatographic stage is used to achieve the separation of two components from a binary mixture, the chromatography is carried out in such a way that the two components are separated in the most complete fashion possible, i.e. in order to obtain a fraction A which only contains very little of compund B and a fraction B which only contains very little of compound A.

In the process according to the invention, the depletion of the epimerized mixture in GPS is, on the contrary, carried out in such a manner as to obtain an excluded fraction containing a roughly equimolecular proportion of GPS and GPM, the other adsorbed fraction being constituted by very pure GPS. By roughly equimolecular is meant from 40 to 60% and more preferably from 45 to 55% of one of the two compounds relative to the total mass of the two compounds. This way of proceeding has the advantage of directly obtaining palatinitol without having to resort to remixing pure fractions of GPM and GPS in appropriate proportions.

The chromatographic fraction containing the excess GPS can be marketed as is after concentration, but it is preferred to crystallize the pure GPS which is then dried.

In fact, GPS is an excellent low cariogenic and low caloric mass sweetening agent being presented in the form of an anhydrous and white crystalline free-flowing powder.

This chromatographic stage is carried out very easily on an industrial scale by application of the hydrogenated mixture on a column loaded with cation exchange resins of a cross-linked sulphonated polystyrene-divinylbenzene type. These resins, in order to be suitable for the chromatography must have a very fine and very homogeneousparticle size, advantageously comprised between 150 and 400 microns, and for their use, are permuted in alkaline or alkaline-earth form. The mixture applied to the column is then fractionated by elution from the resin with water.

Surprisingly, it was noted that whilst GPM and GPS have similar structures and strictly identical molecular weights, the migration of GPM in the resin is much faster, translated as a correlative depletion of GPS in the mixture subjected to chromatography.

From here it is sufficient to extract from the resin, at the start of the elution cycle, the strictly necessary quantity of matter to obtain in a roughly stoichiometric proportion which is that of palatinitol, the components of the mixture subjected to chromatography.

The fraction representing the end of the elution cycle therefore contains a high proportion of GPS, generally comprised between 80 and 95% of dry matter, the remainder being essentially GPM.

This chromatography stage can be carried out in a discontinuous fashion on a single column of resin or on several columns operating in parallel, but it is more advantageously carried out on multicolumn systems connected in a loop, working on the principle of a simulated fluidized bed. These systems have the advantage of obtaining better performances from the resin and of working continuously.

In a general fashion, to obtain the best performances from resins it is preferred to carry out this chromatography at a temperature comprised between 60 and 90° C. As has already been mentioned above, the fraction excluded at the start of the elution cycle, which is depleted in GPS, is advantageously collected in a quantity such that it contains a roughly equimolecular proportion of GPM and GPS. The adsorbed fraction, representing the end of the elution cycle and essentially containing GPS and a little GPM is then concentrated then crystallized under conditions known to the person skilled in the art in order to extract the anhydrous GPS with a view to its marketing.

The fraction collected at the start of the elution cycle and containing GPM and GPS in roughly equimolecular proportions is then, but preferably solely, demineralized on a mixed bed of strong cationic and anionic resins. It is then concentrated, crystallized and dried to produce a commercial powder of palatinitol which is in fact a mixture in roughly equimolecular proportions of anhydrous isomaltitol and GPM dihydrate.

The present invention is illustrated by the following example which is non-limitative, the Applicant only having the purpose of explaining what appears to him to be one of the best means of implementing the process of his invention.

EXAMPLE

First stage:

4 grams of crystallized isomaltose as well as 16 mg of ammonium molybdate $(NH_4)_6 Mo_7 O_{24}$, i.e 0.4% by weight relative to the isomaltose are put in solution in 36 grams of water then the pH of this solution is adjusted to 3.5 using hydrochloric acid.

This solution is then heated to 130° C. for 15 minutes.

After cooling down, this solution is demineralized on a mixed bed of strong cationic and anionic resins which produces an epimerized mixture the resistivity of which is greater than $2.10^6$ ohms. cm.

HPLC chromatography of this epimerized mixture reveals the presence of 35% of α-D-glucopyranosyl-(1→6)D-mannose and 65% of isomaltose. The presence of glucose and mannose are also observed, although in trace amounts.

Second stage:

This epimerized mixture is introduced into a hydrogenation reactor in the presence of 5% by weight of sugars and of Raney nickel. After placing the apparatus under a hydrogen pressure of 50 bars which is maintained throughout the duration of hydrogenation, the contents of the reactor are heated to the temperature of 125° C. The pH of the reaction medium is maintained at 8.0 throughout this hydrogenation using a solution of sodium bicarbonate. Hydrogenation is stopped after 8 hours, when the content of reducing sugars in the reaction medium, measured by the Bertrand method, has become less than 0.1%.

The contents of the hydrogenation reactor are then filtered to remove the catalyst then the syrup is demineralized on a mixed bed of resins, as in the first stage. In this way a perfectly clear and colourless syrup is obtained the composition of which using analysis by gas chromatography proves to be as follows:

isomaltitol: 64.2%

GPM: 34.7%

Third stage:

340 cm$^3$ of the resin marketed under the tradename PCR 732 by the company PUROLITE is introduced into a double jacket glass column thermostatically controlled at 65° C., 2 meters high with an internal diameter of 15 mm. This resin has the following characteristics:

skeleton: cross-linked sulphonated polystyrene-divinylbenzene cross-linking ratio: 7% partcle size: 180 to 280 microns ionic form for use: $Ca^{++}$ 2.5 cm$^3$ of hydrogenated mixture which has been concentrated to 10% is introduced at the top of the column and is then percolated through this resin, being eluted with water at a flow rate of 200 cm³/hour.

After having eluted 169 cm³ of water, a fraction depleted in GPS starts to collect, containing roughly equimolecular proportions of GPS and GPM and representing 78 cm³.

This fraction containing the components of palatinitol in the dissolved state, shows under analysis by gas chromatography a content of 49% GPM and 49.5% GPS.

Immediately following this fraction of palatinitol, a fraction of 81 cm³ is collected constituted by a mixture very rich in GPS, analysis by gas chromatography of which reveals a content of 92% GPS and 7% GPM. This analysis also reveals traces of sorbitol and mannitol.

This stage is carried out 10 times in order to obtain a fraction of adsorbed GPS with an average content of 91.7% and an excluded fraction of a mixture of approximately equal parts of GPM and GPS containing 49.5% GPS and 49.1% GPM.

The adsorbed chromatographic fraction, which is rich in GPS was concentrated under vacuum until a dry matter content of 75% was obtained. On cooling down crystals of anhydrous GPS appear.

The excluded chromatographic fraction, containing 49.1% GPS and 49.5% GPM was concentrated so as to bring its two components to the crystallized state which are then dried in order to obtain a white non-hygroscopic powder of palatinitol titrating 5.1% dampness.

What is claimed is:

1. Process for the preparation of palatinitol, characterized in that:

in a first stage, the epimerization of isomaltose is carried out under conditions which allow a mixture of α-D-glucopyranosyl (1→6)-D-mannose and isomaltose to be obtained, in a second stage, catalytic hydrogenation is carried out on this mixture, in a third stage, chromatographic depletion of the isomaltose in this hydrogenated mixture is carried out so as to obtain a roughly equimolecular mixture of α-D-glucopyranosyl (1→6)-D-sorbitol and α-D-glucopyranosyl (1→6)-D-mannitol.

2. Process according to claim 1, characterized in that the epimerization is carried out in the presence of a hexavalent molybdenum salt.

3. Process according to one or other of claims 1 and 2, characterized in that chromatographic depletion of the isomaltose in the hydrogenated mixture is carried out on cationic resins in alkaline or alkaline-earth form.

4. Process according to claim 3, characterized in that the cationic resins are used in calcium form.

\* \* \* \* \*